US011298566B2

(12) United States Patent
Zacharopoulos et al.

(10) Patent No.: US 11,298,566 B2
(45) Date of Patent: Apr. 12, 2022

(54) SYSTEM, PROCESS AND APPARATUS TO DETERMINE LINAC ISOCENTER

(71) Applicant: AKTINA CORP., Congers, NY (US)

(72) Inventors: Nicholas Zacharopoulos, New City, NY (US); Milan Markovic, Wayne, NJ (US); David Fenyes, Southlake, TX (US)

(73) Assignee: Aktina Corp., Congers, NY (US)

( * ) Notice: Subject to any disclaimer, the term of this patent is extended or adjusted under 35 U.S.C. 154(b) by 0 days.

(21) Appl. No.: 16/934,586

(22) Filed: Jul. 21, 2020

(65) Prior Publication Data
US 2021/0275830 A1 Sep. 9, 2021

Related U.S. Application Data

(60) Provisional application No. 62/986,957, filed on Mar. 9, 2020, provisional application No. 63/033,328, filed on Jun. 2, 2020.

(51) Int. Cl.
*A61N 5/10* (2006.01)
*H05H 9/00* (2006.01)

(52) U.S. Cl.
CPC ......... *A61N 5/1049* (2013.01); *A61N 5/1045* (2013.01); *A61N 5/1082* (2013.01); *A61N 2005/1051* (2013.01); *A61N 2005/1059* (2013.01); *H05H 9/00* (2013.01)

(58) Field of Classification Search
None
See application file for complete search history.

(56) References Cited

U.S. PATENT DOCUMENTS

| 8,353,112 | B2 | 1/2013 | Zacharopoulos et al. | |
| 9,192,784 | B1* | 11/2015 | Ritt | G06T 11/005 |
| 2010/0303210 | A1* | 12/2010 | Beaumont | G01D 18/00 378/207 |
| 2017/0340902 | A1* | 11/2017 | Vilsmeier | A61B 6/4405 |

OTHER PUBLICATIONS

Gibbs et al., "Measurement of mechanical accuracy of isocenter in conventional linear-accelerator-based radiosurgey", Int. J. Radiation Oncology Biol Phys., No. 1 (1993) pp. 117-112.

(Continued)

*Primary Examiner* — Hoon K Song
(74) *Attorney, Agent, or Firm* — Rothwell, Figg, Ernst & Manbeck, P.C.

(57) ABSTRACT

A system to determine the isocenter of a LINAC includes apparatus and processes to determine the axis of rotation for the collimator, the gantry and the patient couch. The system and apparatus enable the tracking of the translation-rotation of mechanical components attached to the LINAC to compute the axis of rotation of Gantry, Collimator and Table. Based on the data collected related to these axis's the LINAC isocenter is determined. The apparatus utilized in the system includes a single emitter module, a signal receiver module, a positioning module. The system also includes a isocenter target module and a gravity module to determine a gravity vector for the LINAC.

12 Claims, 14 Drawing Sheets

(56) References Cited

OTHER PUBLICATIONS

Torfeh et al., "Digital Phantoms for evaluation of software used for an automatic analysis of the Winston-Lutz test in image guided radiation therapy", URL: https://hal.archives-ouvertes.fr/hal-00326648/document (2008) 12 pages.

Heikkila et al., "A Photographic technique for quick assessment of mechanical isocenter of a linear accelerator", Technical Innovations & Patient Supporrt in Radiation Oncology, vol. 2 (2017) pp. 1-4.

Rowshanfarzad et al., "Isocenter verification for linac-based sterotactic radiation therapy: review of principles and techniques" Journal of Applied Clinical Medical Physics, vol. 12, No. 4, (2011) 11 pages.

\* cited by examiner

SYSTEM, PROCESS AND APPARATUS TO DETERMINE LINAC ISOCENTER

CROSS-REFERENCE TO RELATED APPLICATION

The present application claims priority to U.S. Provisional Patent Applications Ser. No. 62/986,957 filed Mar. 9, 2020 and 63/033,328 filed Jun. 2, 2020 which are hereby incorporated herein by reference in entirety for all purposes.

FIELD OF THE INVENTION

Systems, process, devices, apparatus, and methods to track the translation-rotation of mechanical components for determining the Isocenter for a medical linear accelerator (LINAC) by computing the axis of rotation of Gantry, Collimator and Table.

BACKGROUND

Mechanical Rotations

Radiation therapy is a type of cancer treatment that uses beams of intense high energy radiation beams to kill cancer cells.

During treatment, the radiation beams are delivered from a Medical Linear Accelerator (LINAC) to a precise point within the patient.

One of the critical elements of the accuracy of the treatment is the geometrical accuracy of the LINAC mechanical rotations. Each LINAC has three type of rotations that must rotate about a known point in space in order to ensure the most accurate treatment possible. The three rotations are described below.

1. Gantry Rotation. The Gantry [1] rotates about a gantry rotation axis [2]. The gantry can rotate a full 360° around a patient located on the treatment couch [3]
2. Collimator Rotation. The Collimator [4] rotates about the Collimator Axis [5]. The collimator can rotate a full 360°
3. Couch Rotation. The Couch [3] Rotates about the Couch Axis [6]. The Couch [3] is connected to a rotating disk [8] that controls the couch rotation. The couch can typically rotate 180°

Isocenter

Isocenter [8] is defined as the intersection of gantry rotation axis [2], the collimator rotation axis [5] and the couch rotation axis [6]. The accuracy of the patient treatment is very much dependent on the proper determination of the isocenter point in space. Isocenter is a critical concept in radiation therapy: once the patient is position so that the tumor is located at isocenter, the radiation will be fixed at the tumor through gantry, collimator, or table rotation. If isocenter is incorrectly defined, or the tumor is not correctly placed at isocenter and high doses of radiation will be delivered outside the tumor create unwanted adverse side effects.

Mechanical Errors (Walkout)

Ideally each rotating subsystem (Gantry, Collimator, and Table) would rotate through a perfectly circular path in space, created a fixed, unmovable, and precise axis of rotation for each subsystem. This ideal scenario is hardly ever realized, and each rotation can potentially have some mechanical error which effectively blurs the radiation beam. Some of the causes of non-concentric rotation could be noncircular rotational bearings, the effects of gravity on components as they are rotating, and mechanically instability of the moving subsystem. The magnitude of this non-concentricity needs to be measured so that its effects on the precision of the radiation treatment can be estimated.

Non-Coincidence of Axes

Ideally all three axes (Gantry, Collimator, and Table) would intersect in space. There are often separations of the three axes, which then requires an isocenter location to be selected that minimizes the radiation delivery errors over all three axis rotations.

Gravity Direction

Many of the LINAC's components are installed in reference to the earth's gravity direction. For example, the Gantry is installed with its axis of rotation parallel with the earthers horizontal plane, and the treatment couch is installed with its axis of rotation parallel with the earth's vertical plane (perpendicular to gravity). Traditionally, instruments like plumb lines or spirit levels are used.

Treatment Room Lasers

LINAC treatment rooms contain three sets of orthogonal lasers converging at isocenter from the patient's left, right, and from the ceiling above. Patients have small permanent point tattoos placed at the expecting entry point of each laser on their skin. The treatment room lasers are then used to set up the patient for each treatment by aligning them with the patient's tattoos. It is therefore critical for the treatment accuracy that the lasers be properly focused to the machines mechanical isocenter.

SUMMARY

Disclosed is a system including process and apparatus to track the translation-rotation of mechanical components attached to the LINAC to compute the axis of rotation of Gantry, Collimator and Table. All other systems use radiation to determine axes of rotation by acquiring radiation transmission images through a radiation opaque marker as the LINAC components rotate. This is less accurate since it is difficult to decouple radiation steering issues with mechanical rotation issues.

The system disclosed tracks the translation-rotation of mechanical components attached to the LINAC to compute the axis of rotation of Gantry, Collimator and Table. The apparatus and system measure the rotation of each of these three LINAC components, and accurately determines each of the axes from the rotation measurements. The axes are represented by skew lines in 3D space, which are then used to compute the optimal LINAC isocenter.

The disclosed system provides real-time tracking of the mechanical movements of the LINAC. This is currently not possible with the current state of the art apparatuses and procedures. For each of the three rotational axes, the disclosed system shows via software, in 3D and in 2D, the observed tracker position and the computed rotational during rotations. This allows the user to have a very intuitive understanding of how the LINAC is behaving. The system computes the axis "walkout" for each rotational axis. This walkout is defined by the maximum deviation from a perfectly concentric rotation. The system also can measure the direction of gravity so that all of the axis determinations described above are within a coordinate system that is aligned with the Earth's gravity. The system can also align its internal coordinate system with the plane of gantry rotation. This removes the requirement to perfectly align the Signal Receiver with the Gantry.

A Signal Emitter Module with tracking markers is attached to the LINAC gantry and the tracking markers are monitored by the Signal Receiver Module as the Gantry is rotated. As shown on the drawings the signal emitter module is a camera pod which uses stereoscopic cameras and visible light to determine the real-time position and orientation of the rotating components of a (LINAC). However, the position and orientation of the LINAC components could just as effectively be determined using infrared imaging, or by triangulation of ranging systems including RF ranging, laser ranging, lidar, or sonar, or other similar techniques. Once the position and orientation of the gantry, collimator, and table/couch has been determined by any of these methods, the real-time position and orientation of the rotating components of a medical linear accelerator (LINAC) may be derived.

The Signal Receiver Module shown on the drawings is a camera pod with calibrated stereoscopic cameras. The camera pod is positioned on the treatment couch in close proximity to the Signal Emitting Module. The Positioning Module, which is also mounted to the couch, mechanical interconnects to the Camera Pod so that the relative position of the Positioning Module's Target Body is at a reproducible location relative to the Camera Pod. The camera pod defines a coordinate system in space within which the rotational movement the LINAC components can be measured, recorded, and analyzed to compute the LINAC s mechanical rotational axes.

The point of intersection of the all the mechanical axes (commonly referred to as the LINAC isocenter) is determined via software within the camera pod coordinate system with an extremely high level of precision. The system then allows for the precise physical identification this isocenter position in space via an optical tracking tool that can positioned under real-time optical tracking and guidance. This specialized tracking tool provides a real-world target to the mathematically determined isocenter. This physical target to the isocenter is used to define the extremely useful for many situations throughout the LINAC s installation and its routine quality insurance procedures.

The system also incorporates a plumb line that can be measured with the stereoscopic camera pod. This allows for the detection of the earth's vertical direction (gravity) within the camera pod's coordinate system. A correction can be made that aligns camera pod coordinate system to the earth's vertical direction, providing a high level of utility to during LINAC installation, maintenance, and routine quality assurance.

PARTS LIST

Figure 1:
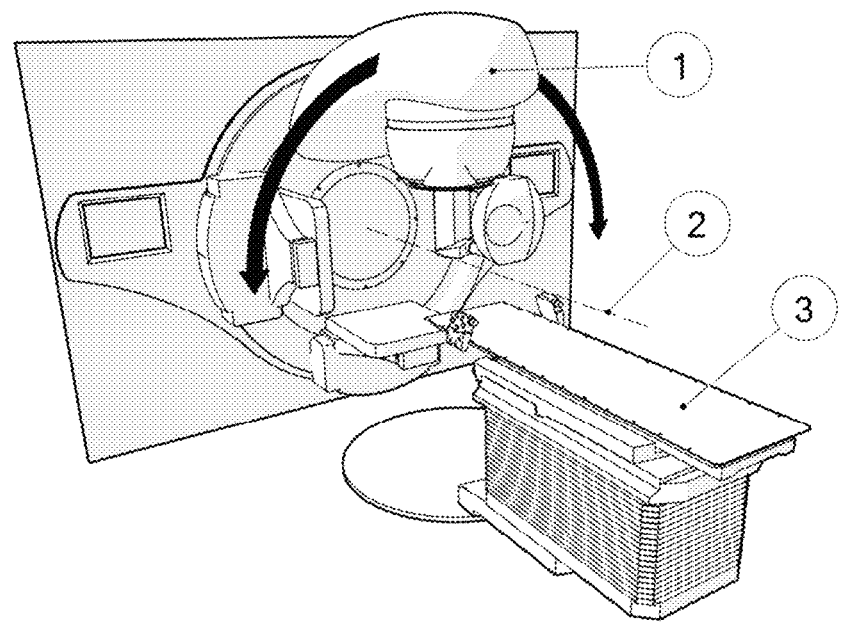
FIG. 1 depicts the Gantry [1] rotation, the gantry axis of rotation [2], and the treatment couch [3].

1. Gantry. The main component of the LINAC which rotates about the patient when delivery radiation during radiation therapy.
2. Gantry axis of rotation. A mathematical construct that represents the axis about which the gantry rotates.
3. Patient Treatment Couch top. Supports the patient during treatment.
4. Collimator. The end of the gantry closest to the patient. The collimator contains jaws which collimate the radiation beam. The collimator can rotate about its own axis to orient the jaws relative to the treatment site.
5. Collimator axis of rotation. A mathematical construct that represents the axis about which the collimator rotates.
6. Couch Axis of rotation. A mathematical construct that represents the axis about which the couch rotates.
7. Not used.
8. Isocenter. The intersection of the gantry, collimator and couch axes. It is the position in space where the patient's tumor or treatment site is positioned during radiation therapy.
9. Not used.
10. Signal Receiving Module/Camera Pod. Acquires stereoscopic images and transmits the images to a computer for processing.
11. Gantry Mount. Mechanically connects the Signal Emitting Module and the Gravity Module to the Gantry.
12. Signal Emitting Module. Mechanically connects to the gantry and emits a signal during gantry, collimator, or couch rotation. These signals are processed by a computer to determine the mechanical axes or rotation of the gantry, collimator or couch.
13. Not used.
14. Signal Emitter. The individual signal emitter of the Signal Emitting Module. These can emit optical light, infrared light, radiofrequency waves, or any signal that can used to determine the position and orientation of the Module.
15. Not used.
16. Not used.
17. Left Camera.
18. Right Camera
19. Not used.
20. Mechanical Interface. Provides a mechanical connection point between the Signal Receiver and the Positioning Module.
21. Isocenter Target Module. Contains signal emitters precisely positioned relative to a radiation opaque marker. The emitters are tracked by the Signal Receiver so that the radiation opaque marker can be positioned with high accuracy to the found isocenter.
22. Positioning Module. Allows for precise manual adjustment of the Isocenter Target Module.
23. Mechanical Interface between Positioning Module and Camera Signal Detector. Ensures that the mechanical connection between the Isocenter Target Module and the Signal Receiver will be controlled and reproducible.
24. Mechanical Interface between Positioning Module and Isocenter Target Module. Ensures that the mechanical connection between the Isocenter Target Module and the Signal Receiver will be controlled and reproducible.
25. Signal Emitter for Isocenter Target Module. The individual signal emitter of the Isocenter Target Module. These can emit optical light, infrared, radiofrequency or any signal that can used to determine the position and orientation of the Pointer.
26. Target Body of the Isocenter Target Module. Encapsulates the radiation opaque marker (typically a sphere of high density metal such as tungsten). Contains crosshairs on the outer surface that are aligned with the sphere within.
27. Z adjustment Knob of the Positioning Module. Provides manual adjustment in the Z direction of the radiation opaque marker.
28. X adjustment Knob of the Positioning Module. Provides manual adjustment in the X direction of the radiation opaque marker.
29. Y adjustment Knob of the Positioning Module. Provides manual adjustment in the Y direction of the radiation opaque marker.
30. Table Clamp. Connects the Positioning Module to the couch.
31. Not used
32. Not used
33. Extension Neck of the Isocenter Target Module
34. Back plate of the Isocenter Target Module.
35. Crosshairs on the Target Body of the Isocenter Target Module. Provide visual indication as to the location of the radiation opaque marker embedded within the Target Body.
36. Radiation Opaque Spherical Target. The spherical target is used to confirm that radiation is being focused properly to the found isocenter. The process of focusing radiation is not described here. This invention is only concerned with positioning the target to the correct location.
37. Gravity Detect Module. Allows for the detection of the direction of gravity.
38. Bayonet Style attachment mechanism of the Gantry Mount
39. Bayonet Style attachment mechanism of the Gravity Module
40. Bayonet Style attachment mechanism of the SEP
41. Not used
42. Not used
43. Bot used 44. Pendulum wire of the Gravity Module. Used as a indicator of the direction of gravity. Image processing techniques compute the wire direction.
45. Pendulum Ball of the Gravity Module. Ensures that the pendulum wire will be taught and aligned with the earth's gravitational field.
46. Compartment for dampening fluid of the Gravity Module. Gets filled with a viscous fluid (water) to dampen the oscillations of the pendulum wire.
47. High contrast background for pendulum wire.
48. Fluid release port.
49. Mounting location for pendulum string
50. Computed center of the emitter. The three-dimensions location, computed through image processing techniques, of the center of the individual emitter. The computer determines this position by combining the found center of the emitter in each left and right image, and then triangulating these positions into three-dimensions.
51. Found center of each individual emitter.
52. Head of the computed emitter vectors
53. Left camera image during gravity image determination. This is a depiction of the image sensor on the left camera.
54. Right camera image during gravity image determination. This is a depiction of the image sensor on the left camera.
55. Pendulum wire as seen from left camera [17]. This is pendulum wire as seen by the camera (projected onto the imaging sensor).
56. Pendulum wire as seen from right camera [18]. This is pendulum wire as seen by the camera (projected onto the imaging sensor).
57. Projection plane of left side pendulum wire. This is a mathematical construct. The focal point of left camera [17] and the pendulum wire on the image sensor create a plane.
58. Projection plane of right side pendulum wire. This is a mathematical construct. The focal point of left camera [17] and the pendulum wire on the image sensor create a plane.
59. Gravity vector determination. Computed from the from intersection of previously computed plane [57] and plane [58]. This
60. Clamping Knob. Used to tighten the Positioning Module to the couch top.

DETAILED DESCRIPTION

The Primary Assemblies/Components of the Disclosed System Are:

Signal Emitting Module

Figure 6:
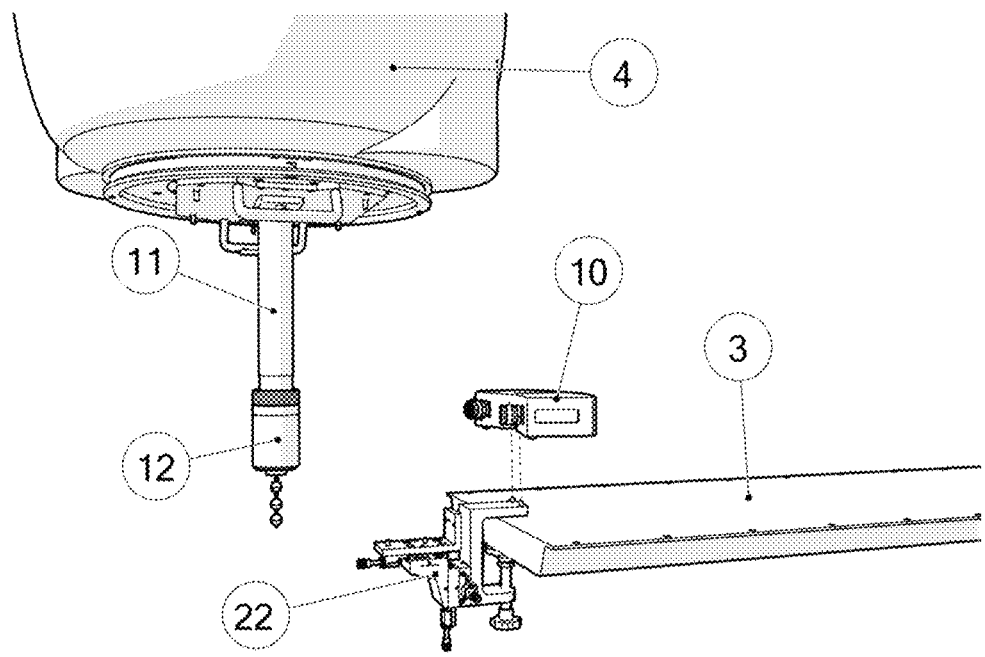
FIG. 6 depicts the Signal Emitting Module [12] connected to the Collimator [4] via the Gantry Mount [11]. The Signal Receiver Module/Camera Pod [10] is shown in position for mounting on Positioning Module [22] attached to the patient treatment couch
Figure 7:
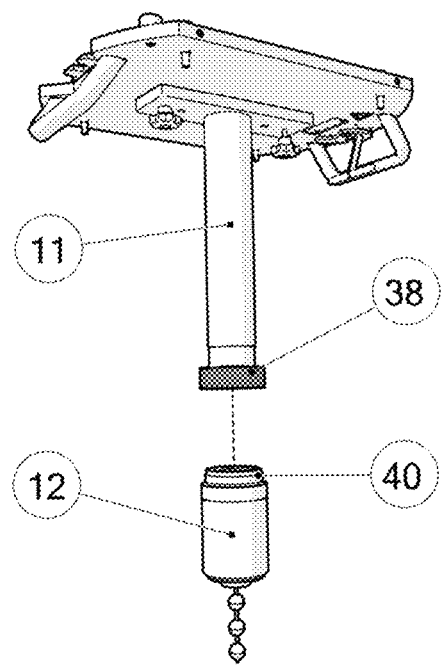
FIG. 7 depicts the Signal Emitting Module [12] connected to the Gantry Mount [11] via a bayonet style mechanism (40) on both the Gantry Mount [38] and the Signal Emitting Module [12].
Figure 8:
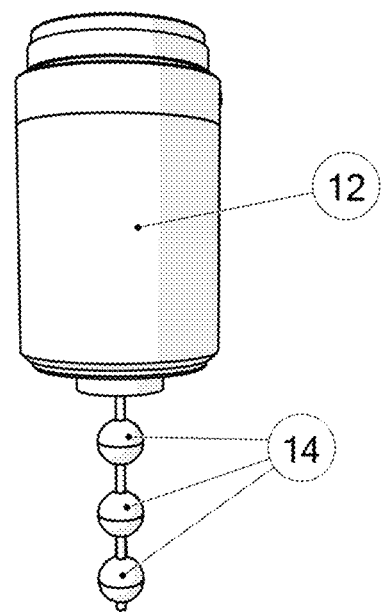
FIG. 8 depicts a side view of the Signal Emitting Pointer [12] showing the spherical emitters [14].

The Signal Emitting Module shown on FIG. 8 contains spherical markers [14] in a fixed orientation. These spherical markers reflect or omit light at a frequency detectable by the Camera Pods [10] detectors (FIG. 6). The Signal Emitting Module rigidly mounts to the LINAC Gantry via a Gantry Mount Mechanism (item [11] in FIG. 6). Once mounted it will rotate with the Gantry, acting as a trackable physical extension to the Gantry itself.

Signal Receiver Module/Camera Pod

Figure 9:
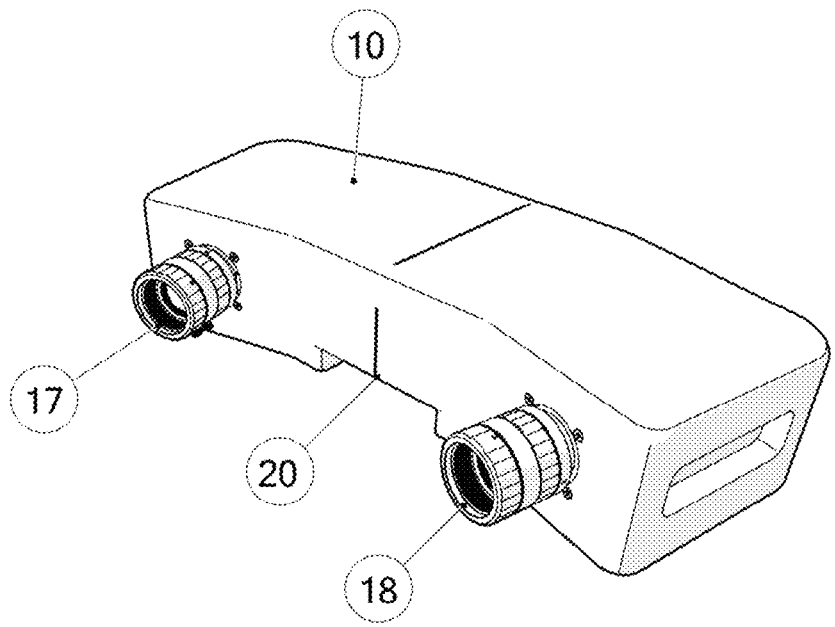
FIG. 9 depicts the Camera Pod showing the Left Camera [17], a right Camera [18], and a mechanical interface [20] to Positioning Module [22]

The Camera Pod 10 (see FIG. 9) contains cameras encased in a rigid outer body in a known fixed orientation to each other. The Camera Pod acquires time-synchronized images and transmits those images to a computer/processor for analysis. With stereoscopic imaging processing techniques, the location and orientation of objects in real space can be determined from the object's found location within each image.

The Camera Pod is positioned on the Couch Top in direct view of the mounted Signal Emitting Module (FIG. 6). This orientation allows for full visibility of the Signal Emitting Module during gantry rotations (see FIG. 1), collimator rotations (see FIG. 2) and couch rotations (see FIG. 3).

Positioning Module

Figure 10:
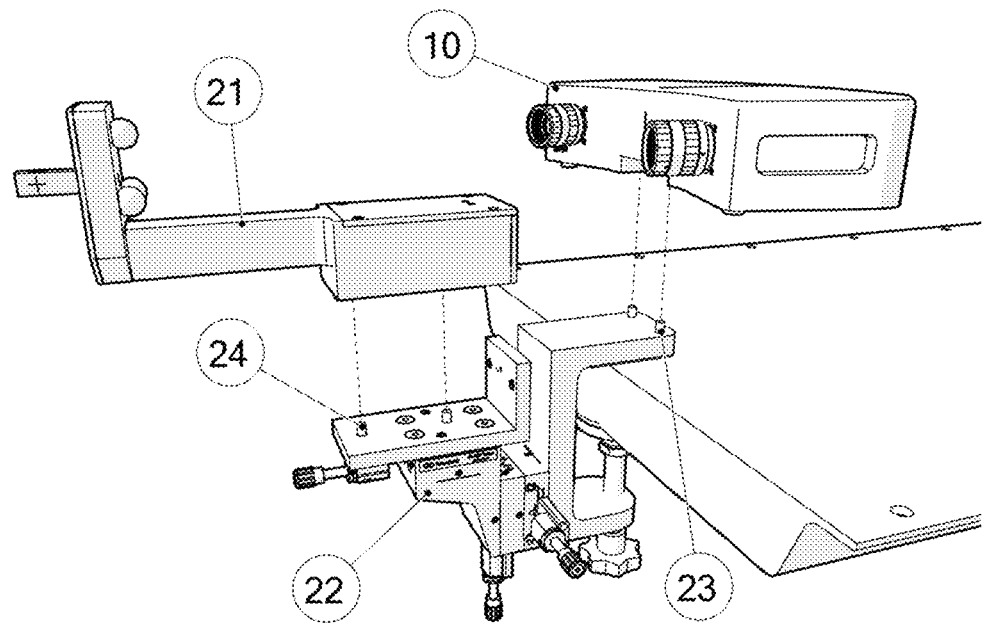
FIG. 10 depicts the Positioning Module [22] mechanically connecting the two components: Isocenter Target Module [21] and Camera Pod [10]. Locating pins on the Positioning Module [23] and [24] ensure a robust and reproducible mechanical interface.

As shown in FIG. 10, the Positioning Module [22] is positioned in front of the couch top. The Positioning Module (22), Camera Pod (10) and Isocenter Target Module (21) are mechanically interfaced when attached to the table, which fixes their relative positions to each other.

The Positioning Module (22) provides a means for adjusting the position of the Isocenter Target Module (21) relative to the Camera Pod (10). It contains three manual adjustment knobs (items [27], [28] and [29] in FIG. 13) which independently adjust the Isocenter Target Module in three cartesian directions.

Isocenter Target Module

The purpose of the Isocenter Target Module (21) is to position a physical target to the found isocenter location, thus creating a real-world reference to a mathematical position previously only existing within Camera Pod's coordinate system. Once positioned at the isocenter, x-ray images of LINAC generated radiation beams passing through the target can be used to steer the LINAC's radiation to the center of the spherical target (resulting in congruence of the LINAC's radiation to its own mechanical isocenter). Crosshairs on the Target Body can then also be used to adjust the treatment room patient setup lasers so that they also align with the found Isocenter. The Isocenter Target Module ([21] in FIG. 11) is positioned on the Positioning Module [22]. It contains spherical emitting markers [25] in fixed known positions. The emitters are visible by the Camera Pod and are used to determine its position and orientation within the Camera Pods coordinate system. The spherical emitter locations are accurately controlled relative the radiation opaque target (usually a high-density metal sphere) contained within Target Body [26].

Figure 16:
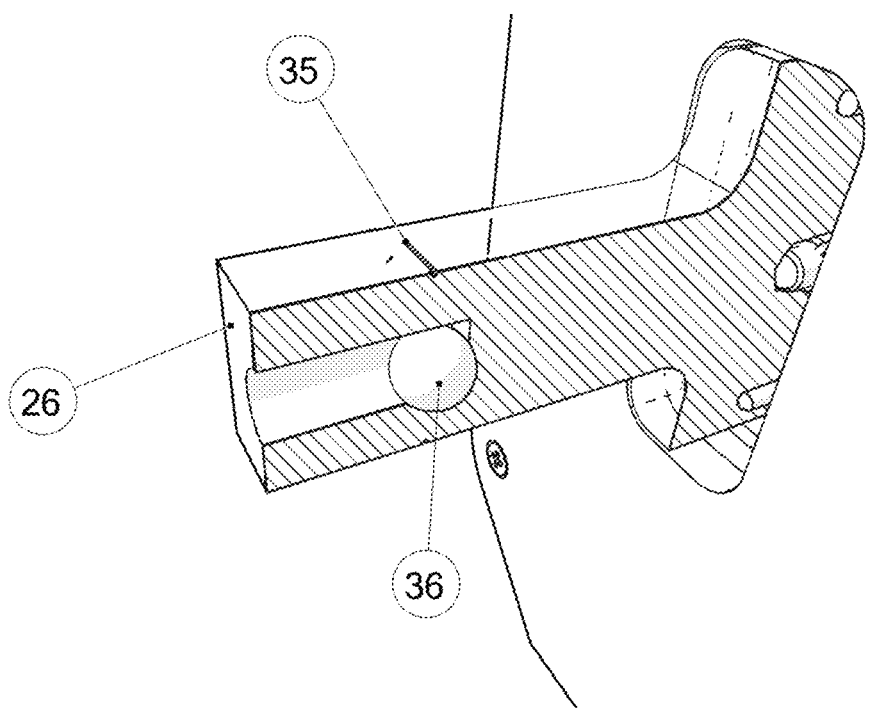
FIG. 16 depicts a cross-section of the Isocenter Target Module showing the Radiation Opaque Marker [36] which is aligned with the external crosshairs [35] that are etched on the target body [26].

The target body [26], shown in cross-section on FIG. 16, contains an embedded radiation-opaque spherical target [36] aligned with external crosshairs on the outer surface [35].

Gravity Detection Module

Figure 18:
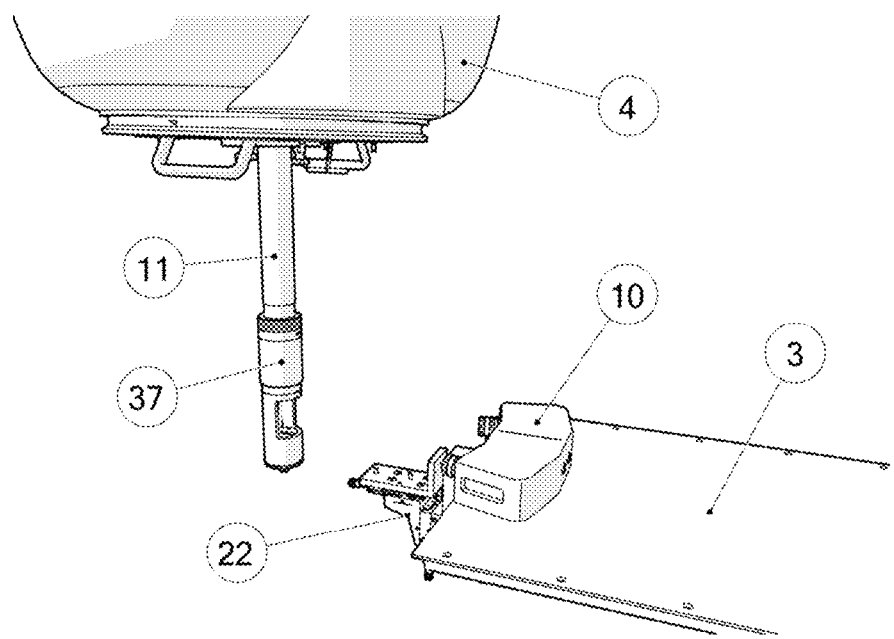
FIG. 18 depicts the Gravity Detect Module (Gravity Module) [37] in typical use configuration connected to the Gantry Mount [11]. The Target Module [21] is removed from the Positioning Module [22] so as not to interfere with the Gravity Module [37]. The Camera Pod [10] is positioned on the Couch top [3] as it monitors the Gravity Module [37].
Figure 19:
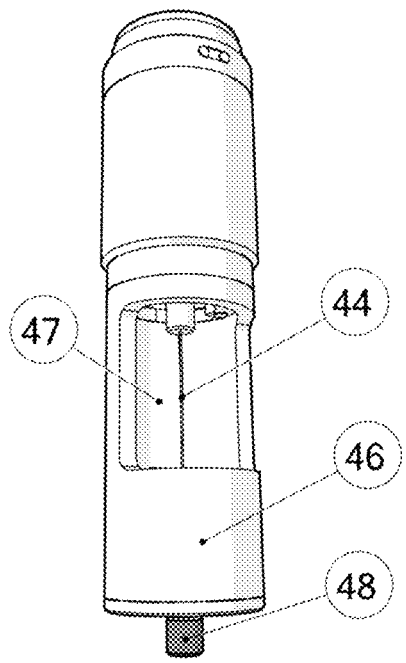
FIG. 19 depicts the Gravity Detect Module showing the pendulum wire [44], compartment for dampening fluid [46], high contrast background [47], and fluid release port [48].
Figure 20:
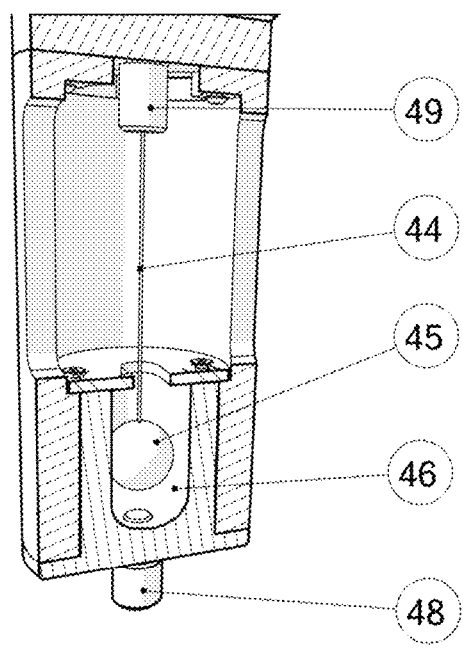
FIG. 20 depicts a cross-section view of the Gravity Detect Module: Pendulum wire [44], Pendulum Ball [45], Compartment for dampening fluid [46], Fluid Release Port [48], Mounting location for pendulum string [49]

The Gravity Module [37] (FIG. 18) connects to the Gantry Mount [11] in an identical manner and location as the Signal Emitting Module so that it also can be imaged by the Camera Pod [10]. As can be seen in FIG. 19, it contains a plumb wire [44] that is visible by the Camera Pod through an opening in its outer casing. The plumb wire is held taught by a weight ([45] in FIG. 20) at its end and a vessel of fluid surrounding the weight dampens its oscillations (see cross-sectional view in FIG. 20).

The System Process Utilized to Determine the Real-Time Position and Orientation of the Rotating Components of a Medical Linear Accelerator (LINAC) Are:

Determining the Gantry Axis

Figure 21:
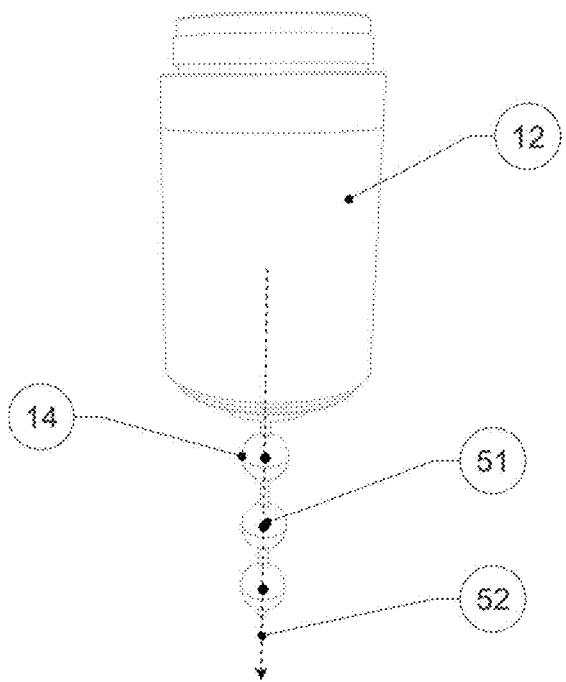
FIG. 21 depicts the Signal Emitting Module [12] with individual Signal Emitters [14], computed emitter centers [51] and computed emitter position/orientation [52].
Figure 22:
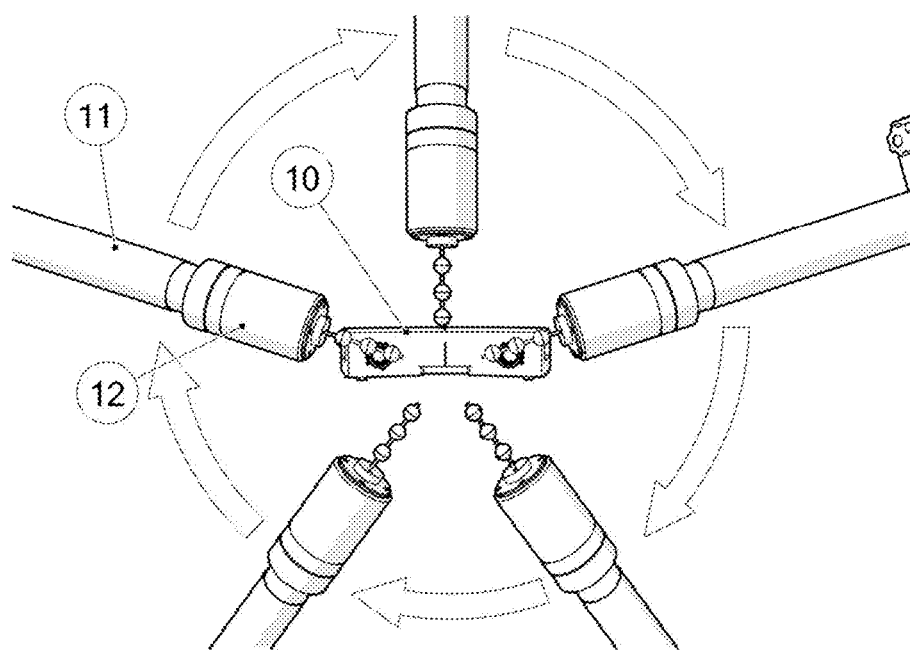
FIG. 22 depicts an example of six images captured by the Camera Pod [10] as the Signal Emitting Pointer [12] rotates while connected the Gantry Mount [11].
Figure 23:
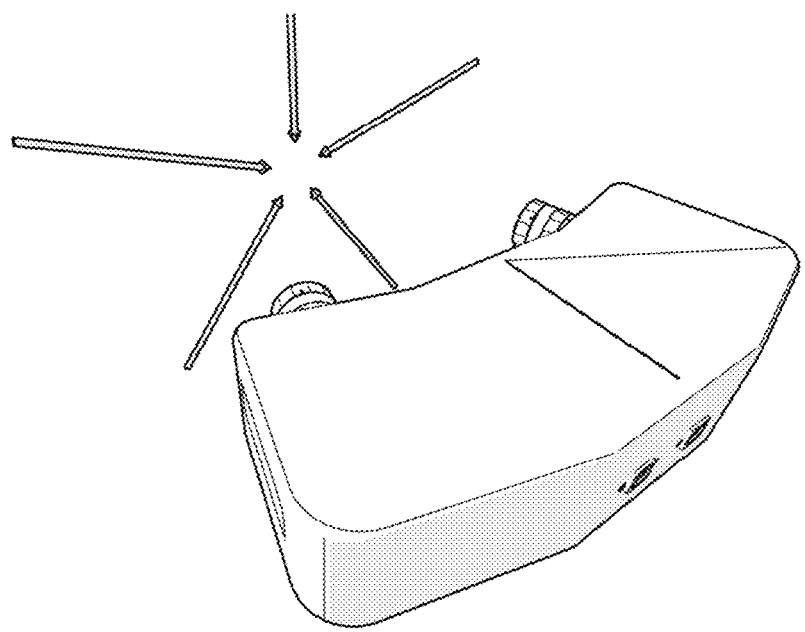
FIG. 23 depicts signal Emitting vectors computed from the positions of the Signal Emitting Module shown in FIG. 22.
Figure 24:
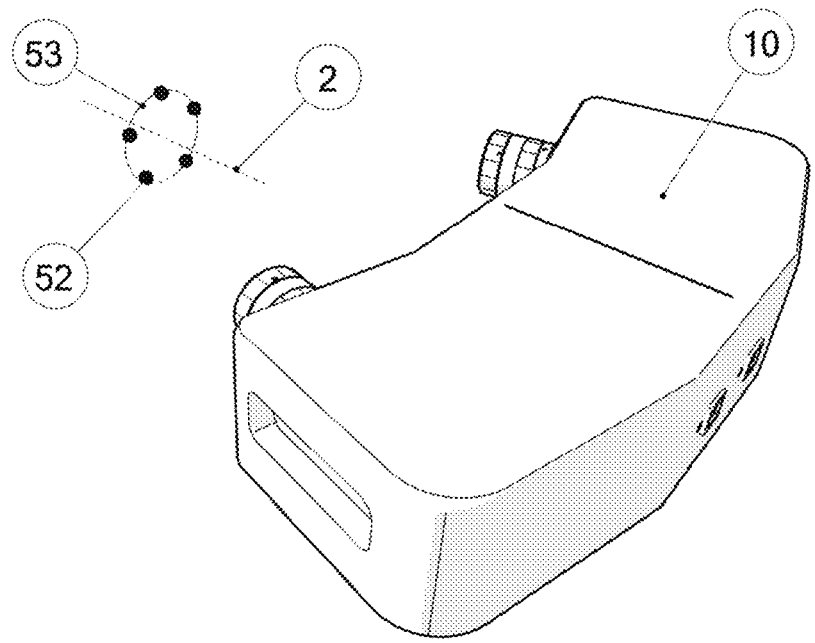
FIG. 24 depicts the found emitter vector heads [52] and the optimized fit [52] of the vector head. The normal to the optimized fit will produce the axis of rotation [2].

1. A Signal Emitting Module [12] is attached to a Linear Accelerator Gantry [4] via a Gantry Mount [11] as shown in FIG. 6. A Signal Receiver [10] is positioned on the LINAC couch [3] in a position to acquire stereoscopic images of the Signal Emitting Module [12] as the Gantry rotates.
2. The Gantry ([1] in FIG. 1) is rotated through its mechanical rotation while the Signal Receiver [10] captures images of the Signal Emitting Module [12] at regular time intervals. An example of five acquisitions over a 360° rotation is shown in FIG. 22.
3. For each acquisition, images pairs from the left camera and right camera are sent from Signal Receiver [10] to a computer to determine the location and orientation of the Signal Emitting Module in three-dimensions. Image process techniques locate the center of each individual emitter (see [51] in FIG. 21) in each image. Stereoscopic image process techniques then compute the three-dimensions coordinates of each individual signal emitter from its location in the left and right-sided images. The group of three-dimensional positions of all the individual signal emitters and then registering against the expected individual emitter locations. This registration process is used to determine the orientation and location of the Signal Emitting Module for each acquisition (shown as [52] in FIG. 21).
4. The location of Signal Emitting Module from all data acquisitions (see FIG. 24) are then fit to a three-dimension circular path, the central axis of which represents the gantry axis of rotation ([2] in FIG. 1).

Determining the Collimator Axis of Rotation

1. The system is configured as described in Section 5.
2. The identical steps described in Section 5 are followed except that instead of rotating the Gantry, the collimator ([4] in FIG. 2) is rotated.
3. The identical image processing and data analysis steps described in Section 5 are followed to determine the collimator axis of rotation ([5] in FIG. 2).

Determining the Couch Axis of Rotation

4. The system is configured as described in Section 5.
5. The identical steps described in Section 5 are followed except that instead of rotating the gantry, the couch is rotated ([3] in FIG. 3).
6. The identical image processing and data analysis steps described in Section 5 are followed to determine the couch axis of rotation ([6] in FIG. 3).

Determining the Ideal Mechanical Isocenter

Figure 25:
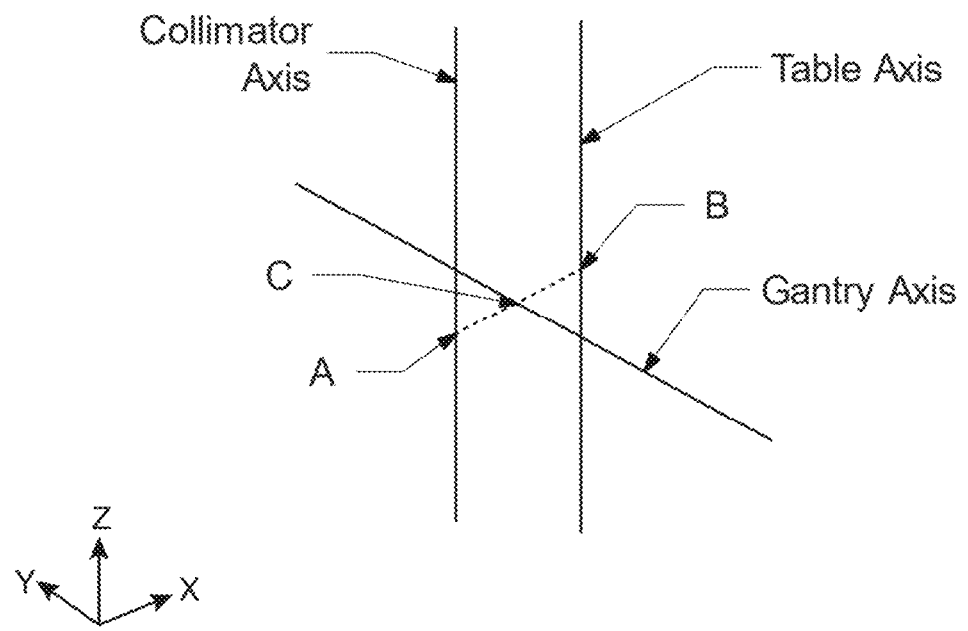
FIG. 25 is an example of LINAC isocenter based on the Gantry, Collimator, and Table axes of rotation.
Figure 26:
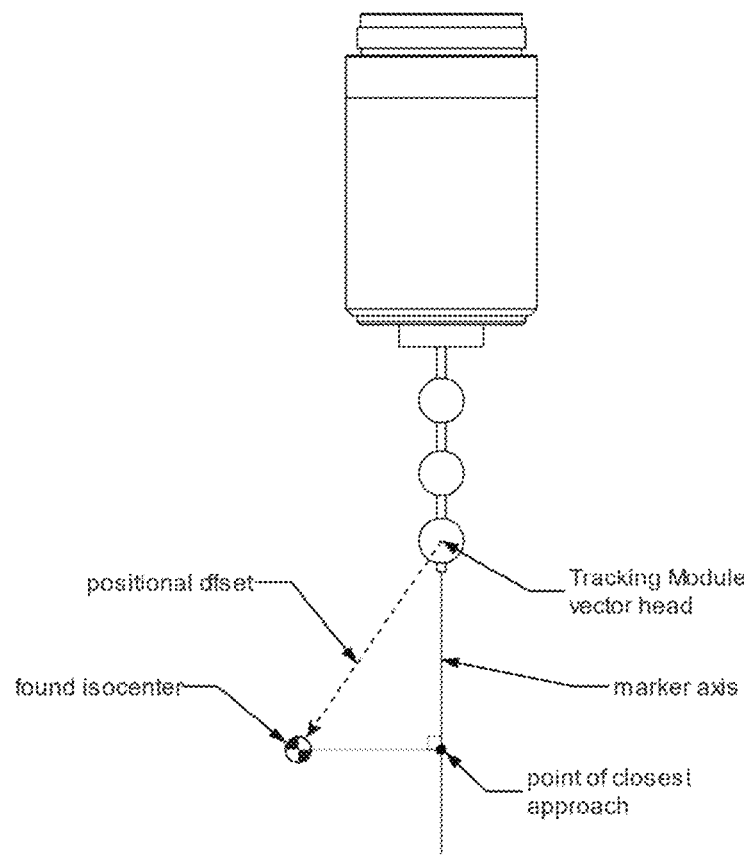
FIG. 26 is an example of positional offset vector.
Figure 27:
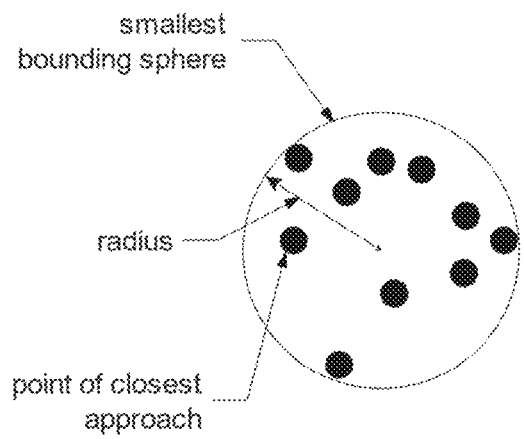
FIG. 27 is an example of walkout radius determined from bounding sphere for all points of closest approach.

1. Once all three axes are determined (Gantry, Collimator, and Couch), a software algorithm determines the ideal position of the LINAC Isocenter by finding the location in space that would minimize the maximum error from radiation delivered to the patient through any of the LINAC's mechanical movements.
2. The Gantry Axis of rotation (which is oriented in the patient head-to-foot direction) is perpendicular to the two Collimator and Couch axes (which are oriented in a floor-to-ceiling direction). In an ideal scenario, all three axes would intersect. The intersection point is the Isocenter. Typically, the axes do not all meet at the same point. Therefore, ideal isocenter must be then selected so that its position minimizes the maximum distance error for the radiation beam to the target for all mechanical rotations. Maybe we move this paragraph to background section
3. The following relations can be used to compute the LINAC isocenter (see FIG. 25):
1. The Z height of the LINAC isocenter is set to the gantry axis Z position. This is because the collimator and couch rotation axes are defined in the X-Y plane.
2. The X position of the LINAC isocenter is set to the midpoint of the two extreme X values between all three axes.
3. The Y position is computed from the midpoint between the Y locations of the collimator and couch rotation axes.
4. Other rules can also be used that prioritize one axes over the others (for example, a weighted approach).

Positioning a Target Marker at Isocenter

Figure 11:
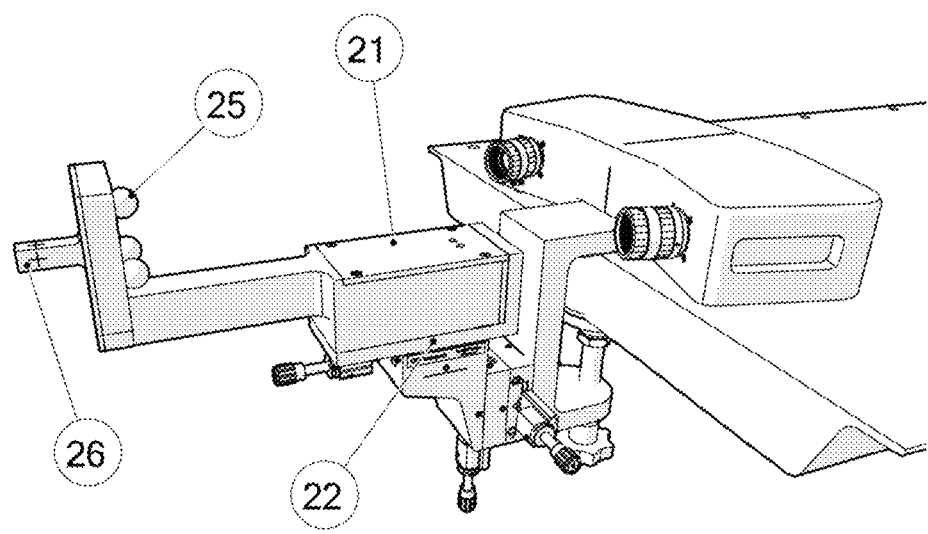
FIG. 11 depicts the Isocenter Target Module [21] seated within the Positioning Module [22]. The Camera Pod monitors the Signal Emitters of the Isocenter Target Module [25] in order to precisely position the Target Body [26] to isocenter.
Figure 12:
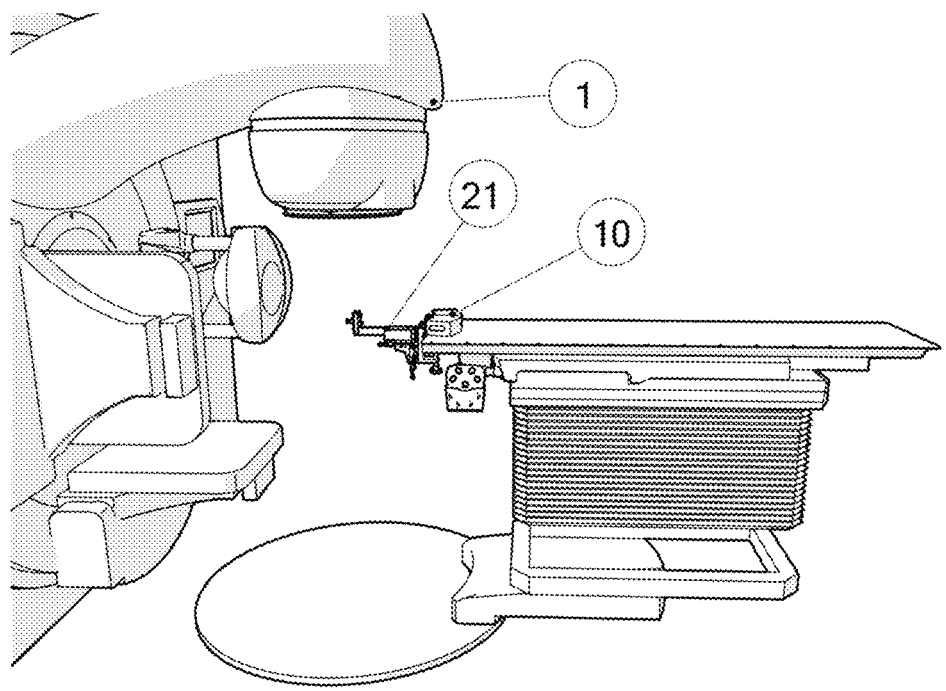
FIG. 12 depicts the Isocenter Target Module [21] positioned beneath the Gantry [1] within the radiation field. The Camera Pod [10] is positioned on the Couch and tracks the position/orientation of the Isocenter Target Module [21].
Figure 13:
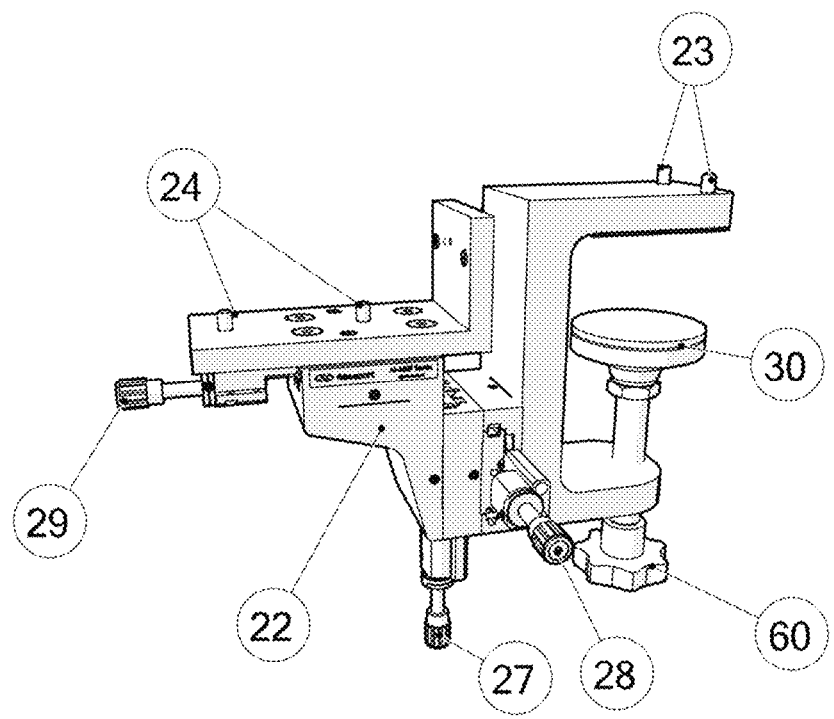
FIG. 13 depicts the components of the Positioning Module [22]: Z adjustment Knob of the Positioning Module [27], X adjustment Knob of the Positioning Module [28], Mechanical Interface between Positioning Module and Camera Pod [23], Y adjustment Knob of the Positioning Module [29], Clamping Knob [60], Table Clamp [30], Mechanical Interface between Positioning Module and Isocenter Target Module[24].
Figure 14:
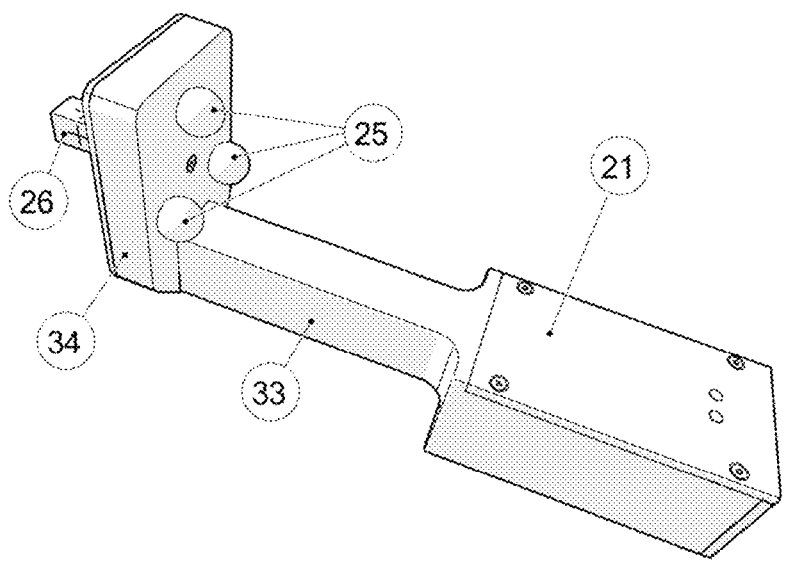
FIG. 14 depicts the components of the Isocenter Target Module[21], rear view: Signal Emitters [25], Target Body [26], Back plate [34], and Extension Neck [33].
Figure 15:
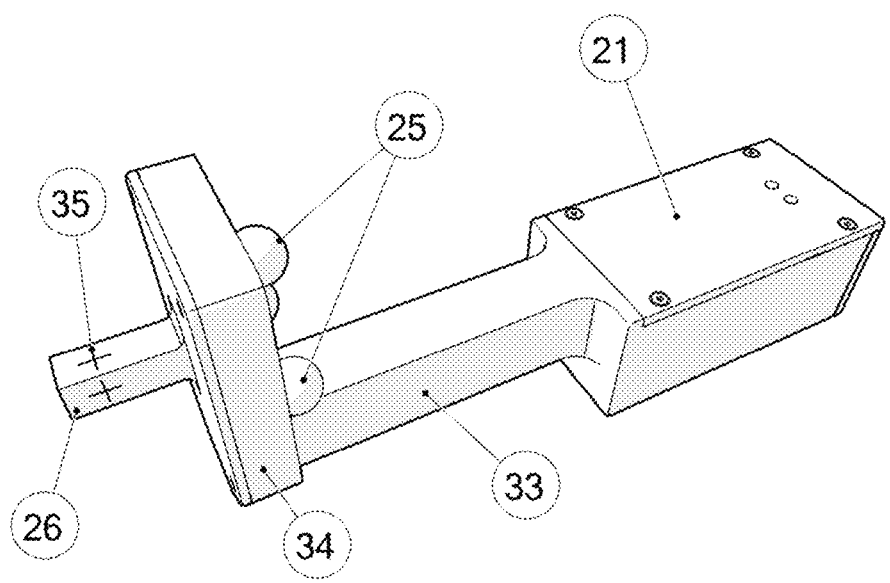
FIG. 15 depicts the components of the Isocenter Target Module, front view: Signal Emitter for Isocenter Target Module[25], Target Body of the Isocenter Target Module [26], Back plate of the Isocenter Target Module[34], Extension Neck of the Isocenter Target Module[33], Crosshairs on the Isocenter Target Module[35].

1. Once the isocenter is determined, a target marker can be positioned to isocenter (this is useful since tests must performed that confirm that radiation is properly focused towards mechanical isocenter).
2. Without disturbing the Camera Pod [10] and the Positioning Module [22] from the setup used to determine isocenter (this will ensure the identical coordinate system), The Isocenter Target Module [21] is positioned on the Positioning Module as shown in FIG. 11.
3. The Isocenter Target Module consists of a set of signal emitters ([25] in FIG. 11) positioned precisely relative to a radiation opaque spherical marker [36] embedded within a target body 26.
4. The Signal Receiver [10] is set to capture images of the Isocenter Target Module's Isocenter Target Module's signal emitters [25]. These images are sent to a computer to determine the location of the Isocenter Target Module in three-dimensions through imaging processing techniques identical to those used for gantry axis determination. Summarized again here These images are analyzed to find the center of each individual emitter (see [51] in FIG. 21) in three-dimensions coordinates. The Isocenter Target Module's position and orientation in space are then determined registering those found locations against the expected locations individual emitter locations. This registration process is used to determine the orientation and location of the Signal Emitter for each acquisition.
5. For each image pair acquisition, the found location of the Isocenter Target Module's radiation opaque spherical marker is compared to found isocenter and the software instructs the user how to shift the Isocenter Target Module in three dimensions to align the two positions. FIG. 13 shows the X dial [28], the Y dial [29], and the Z dial [27] that can be used to accomplish these shifts. The software provides real-time feedback to guide the user during this process.

Adjustment of the Room Lasers

Figure 2:
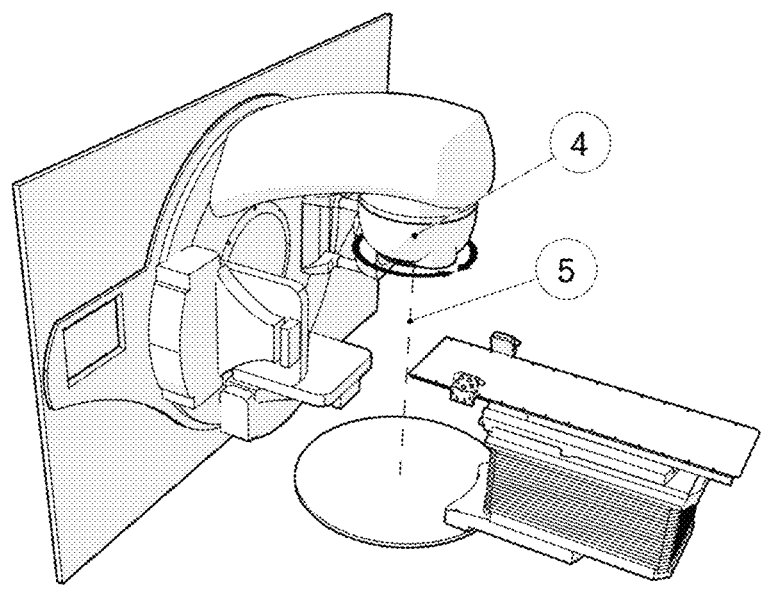
FIG. 2 depicts the collimator [4] rotation about the collimator axis of rotation [5].
Figure 3:
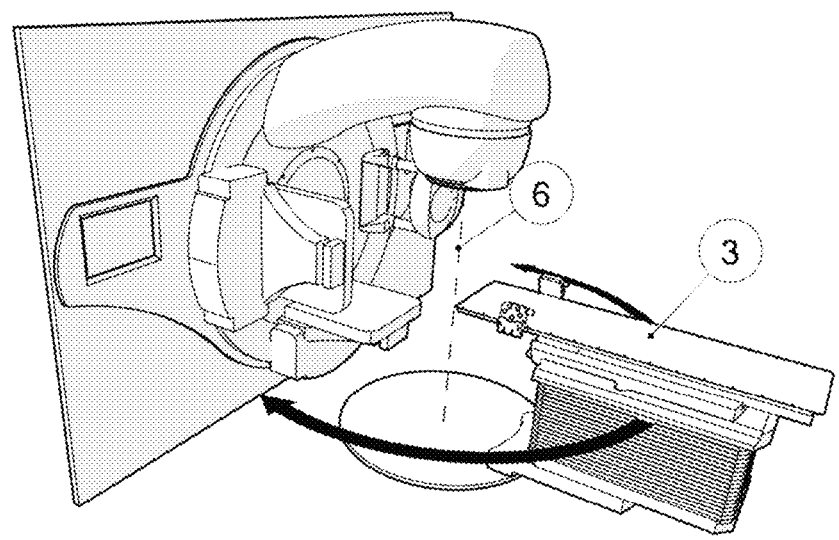
FIG. 3 depicts the couch [3] rotation about the couch axis of rotation [6].
Figure 4:
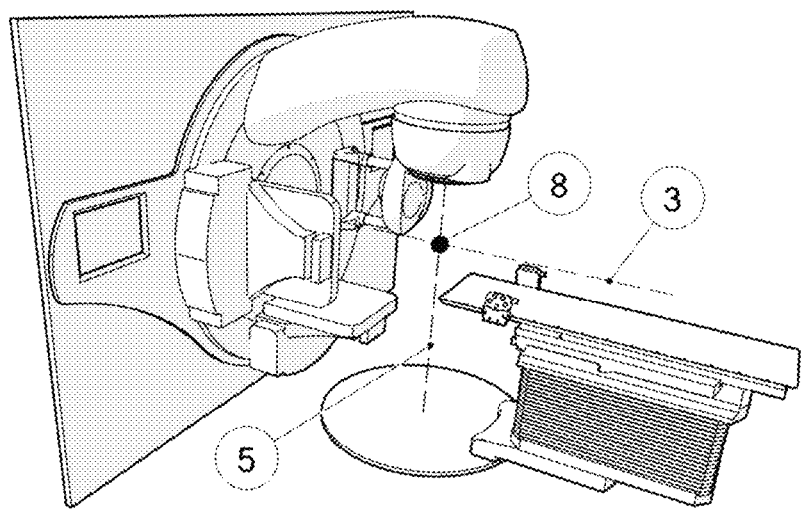
FIG. 4 depicts the isocenter [8] as the intersection of the gantry axis of rotation [3] and the collimator and couch axes of the rotation [5].
Figure 5:
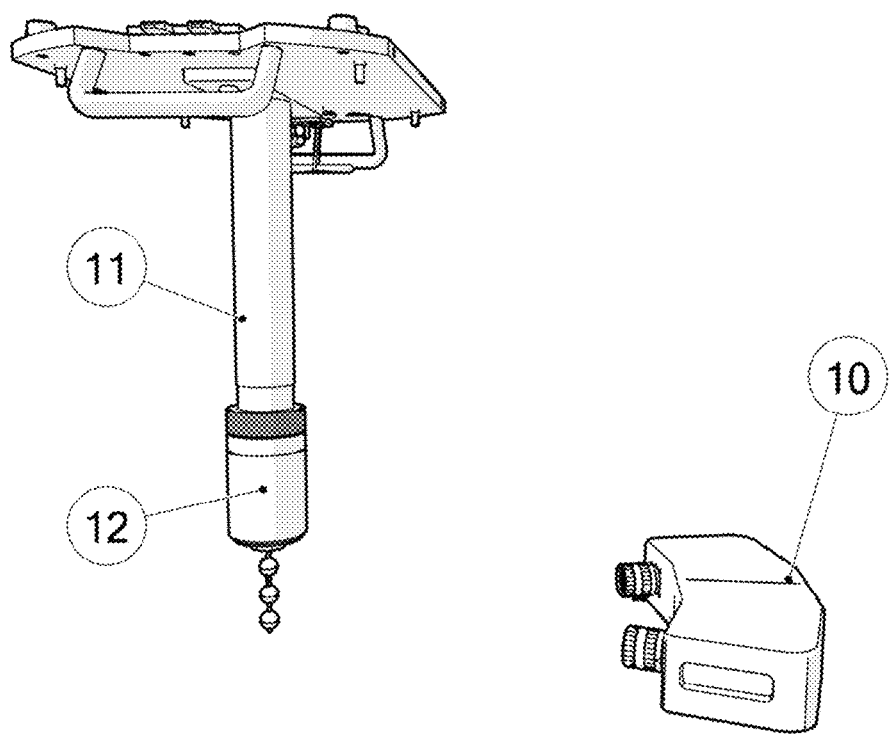
FIG. 5 depicts the Gantry Mount [11] and the Signal Emitting Module [12] mounted on the Gantry Mount (11) and the Signal Receiver Module/Camera Pod [10]

1. The target body [26] of the Isocenter Target Module contains a radiation opaque spherical marker [36] which is embedded in a position orthogonally aligned with the four sets of cross-hairs [35] scribed on the outer surfaces (see cross-sectional view in FIG. 16). FIG. 16
2. The crosshairs on the outside of the target body allow room laser to be adjusted so that they precisely align with the radiation opaque sphere located inside (which is not visible).
3. Once the radiation opaque sphere [36] is aligned with the found isocenter (described in the steps above), the left, right, and top room lasers are manual adjusted so that they are focused on the crosshairs present on left, right, and top of the target body ([26] in FIG. 11)

Determining the Direction of Gravity

Figure 17:
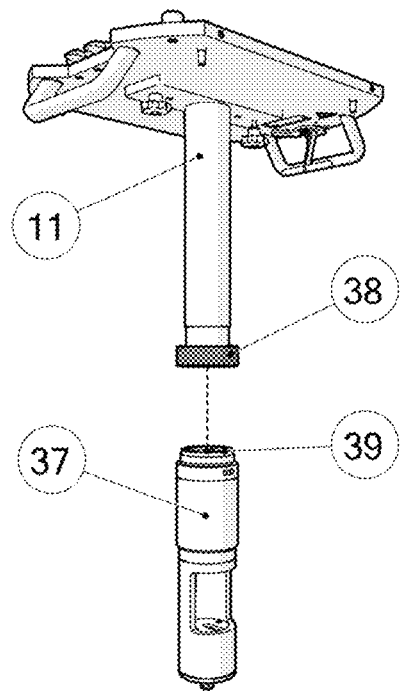
FIG. 17 depicts the Gravity Detect Module [37] mounted to the Gantry Mount [11] with bayonet style connections [39] and [38].
Figure 28:
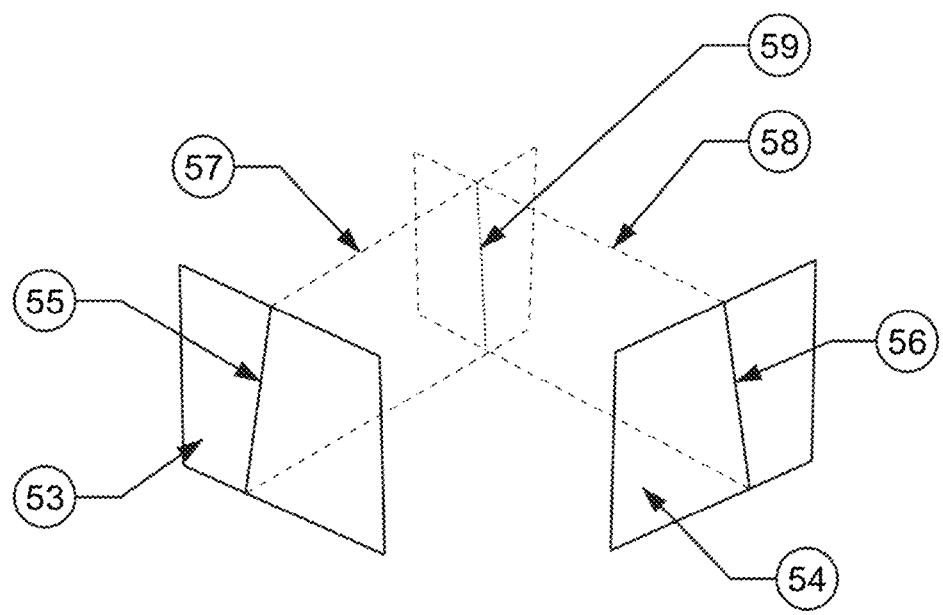
FIG. 28 is a depiction of gravity vector [59] determined via the intersection of intersection of [57] and [58]: Left camera image during gravity image determination [53], Right camera image during gravity image determination [54], Pendulum wire as seen from left camera [55], Pendulum wire as seen from right camera [56], Projection plane of left side pendulum wire from focal point of left camera [57], Projection plane of right side pendulum wire from focal point of left camera [58].

1. Instead of using a typical spirit level to align the gantry level with the earth's gravitational field, a Gravity Module [37] shown in FIG. 17 can be connected to the LINAC via the Gantry Mount [11].
2. The Gravity Module shown in cross-section in FIG. 20 contains a pendulum ball [45] suspended by a flexible wire [44]. The pendulum ball is surrounded a viscous fluid (typically water) contained within a vessel [46]. The fluid rapidly dampens oscillations of the ball (without the dampening fluid, the time required for the pendulum to stop oscillating would be prohibitive).
3. The Signal Receiver acquires image pairs of the gravity module and uses signal processing techniques to determine the direction in space of the pendulum wire, which correlates to the direction of the gravity vector.
4. FIG. 28 shows a graphical description of the mathematical process used: the pendulum wire [44] is detected within the left image [53] and right image [56] acquired by the Camera Pod.
5. The pendulum wire line is mathematically projected out from the camera focal point to create left-sided plane [55] and a right-sided plane [58]
6. The intersection of the two planes is computed and represents the direction of the gravity vector [59].

Software Overview
1. Initialize a coordinate system that correlates to real-world coordinates of the Tracking Module,
2. Present Tracking Module location in real-time (both in 3D view and 2D projections).
3. Show the Tracking Module position and direction when recording a rotation.
4. Compute the direction of gravity within the previously initialized coordinate system.
5. Compute the rotational axes (Gantry, Collimator or Table).
6. Show the positions of the computed axes in a 3D view and in 2D projections.
7. Compute the LINAC isocenter based on the three computes axes.
8. Show the LINAC isocenter in 3D and 2D views.
9. Create reports for presenting the LINAC rotational axes and LINAC isocenter.
10. Store previous datasets to allow for post-processing and data review.
11. Uses the walkout radii of each of the three axes to compute an overall LINAC walkout radius.

The LINAC Isocenter determination process includes mounting a signal emitter module on a gantry; mounting a signal receiver module in line with the signal emitter module on a positioning module mounted on a couch; determining the an axis of rotation for the gantry by rotating the gantry with the signal receiver module receiving signals from the signal emitter module during the gantry rotation; determining an axis of rotation for a collimator by rotating the collimator with the signal receiver module receiving signals from the signal emitter module during the collimator rotation; determining an axis of rotation for a couch by rotating the couch with the signal receiver module receiving signals from the signal emitter module during the couch rotation; and determining the LINAC isocenter by processing the signals received for the axis of rotation for the gantry the axis, and the collator.

In one embodiment the LINAC Isocenter determination process the signal emitter module emits light signals and the signal receiver module receives the light signals. But as stated other signal sources can be utilized such as infrared imaging, or by triangulation of ranging systems including RF ranging, laser ranging, lidar, or sonar, or other similar techniques such as utilizing laser beams.

The signal emitter module comprises a minimum of one marker reflecting or omitting light at a specific frequency optimized for the signal receiver.

The LINAC Isocenter determination process can also include mounting an isocenter target module on the positioning module and positioning with an isocenter target marker located in the isocenter target module at the LINAC isocenter. The isocenter target module includes a minimum of one target marker.

In one embodiment the positioning module includes a joystick movement to adjust the X, Y, and Z positions.

The isocenter target module can include a radiation opaque spherical marker inside a target body and cross hairs on an outside of the target body. This allows lasers to be adjusted by focusing on the LINAC isocenter.

The LINAC Isocenter determination can utilize a processor to collect data and process it utilizing software.

In one embodiment a gravity module is mounted on the gantry the camera pod acquire images of location of the gravity module to be used in determine the direction of a gravity vector.

In another embodiment the signal receiver module is fixed on couch and signal emitter module mounted on the gantry.

Having described preferred embodiments which serve to illustrate various concepts, structures and techniques which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims.

We claim:
1. A LINAC Isocenter determination process comprising:
mounting a signal emitter module on a gantry;
mounting a signal receiver module in line with the signal emitter module on a positioning module mounted on a couch;
determining an axis rotation for the gantry by rotating the gantry with the signal receiver module receiving signals from the signal emitter module during the gantry rotation;
determining an axis of rotation for a collimator by rotating the collimator with the signal receiver module receiving signals from the signal emitter module during the collimator rotation;
determining an axis of rotation for the couch by rotating the couch with the signal receiver module receiving signals from the signal emitter module during the couch rotation; and
determining the LINAC isocenter by processing the signals received for the axis of rotation for gantry, the collator, and the couch.

2. A LINAC Isocenter determination process according to claim 1 wherein the signal emitter module emits light signals and the signal receiver module receives the light signals.

3. A LINAC Isocenter determination process according to claim 2 wherein the signal emitter module comprises a minimum of one marker reflecting or omitting light at a specific frequency optimized for the signal receiver module.

4. A LINAC Isocenter determination process according to claim 3 wherein the signal receiver module is a camera pod.

5. A LINAC Isocenter determination process according to claim 4 wherein the camera pod is comprised of at least 2 cameras capable acquiring of time synchronized images for computer analysis.

6. A LINAC Isocenter determination process according to claim 4 further comprising mounting a gravity module on the gantry and using the camera pod to acquire images of location of the gravity module to be used in determine a direction of a gravity vector for a LINAC.

7. A LINAC Isocenter determination process according to claim 6 wherein the gravity module is composed of a pendulum ball surrounded by viscous fluid contained in a vessel.

8. A LINAC Isocenter determination process according to claim 1 further comprising mounting an isocenter target module on the positioning module and positioning the isocenter target module at the LINAC isocenter using at least one spherical emitter marker on the isocenter target module.

9. A LINAC Isocenter determination process according to claim 8 wherein the isocenter target module includes a radiation opaque spherical marker inside a target body and crosshairs on an outside of the target body and further comprising adjusting treatment room lasers to focus on the LINAC isocenter.

10. A LINAC Isocenter determination process according to claim 1 further comprising utilizing a processor to collect data and process it utilizing software.

11. A LINAC Isocenter determination process according to claim 1 wherein the positioning module includes separate controls for an X position, a Y position, and a Z position.

12. A LINAC Isocenter determination process according to claim 1 wherein the positioning module includes a joystick movement to adjust the X, Y, Z positions.

* * * * *